US008177758B2

(12) United States Patent  
Brooks, Jr. et al.

(10) Patent No.: US 8,177,758 B2
(45) Date of Patent: May 15, 2012

(54) PNEUMATIC INJECTOR

(75) Inventors: William Woodrow Brooks, Jr., Rochester, MN (US); Donald John Wanek, Rochester, MN (US)

(73) Assignee: Rochester Area Consulting Engineers (RACE), Rochester, MN (US)

( * ) Notice: Subject to any disclaimer, the term of this patent is extended or adjusted under 35 U.S.C. 154(b) by 498 days.

(21) Appl. No.: 12/420,134

(22) Filed: Apr. 8, 2009

(65) Prior Publication Data

US 2010/0262082 A1   Oct. 14, 2010

Related U.S. Application Data

(60) Provisional application No. 61/043,268, filed on Apr. 8, 2008.

(51) Int. Cl.
A61M 5/31 (2006.01)

(52) U.S. Cl. ........ 604/193; 604/146; 604/187; 604/200; 604/506

(58) Field of Classification Search .................. 604/506, 604/193, 187, 200, 146, 141, 143, 184, 194, 604/196, 204, 214, 218, 221, 222, 226, 311
See application file for complete search history.

(56) References Cited

U.S. PATENT DOCUMENTS 6,517,517 B1    2/2003  Farrugia et al.
2010/0318035 A1*  12/2010  Edwards et al. .............. 604/187
* cited by examiner Primary Examiner — Jackie Ho
Assistant Examiner — Michael J Anderson
(74) Attorney, Agent, or Firm — Schwegman, Lundberg & Woessner, P.A.

(57) ABSTRACT

This document discloses, among other things, an air-powered auto-injector device for subcutaneous delivery of a rescue drug. The device is configured for self-administered treatment of anaphylactic shock. Air is compressed by relative movement of a piston and a cylinder and released to subcutaneously drive an hypodermic needle.

8 Claims, 10 Drawing Sheets

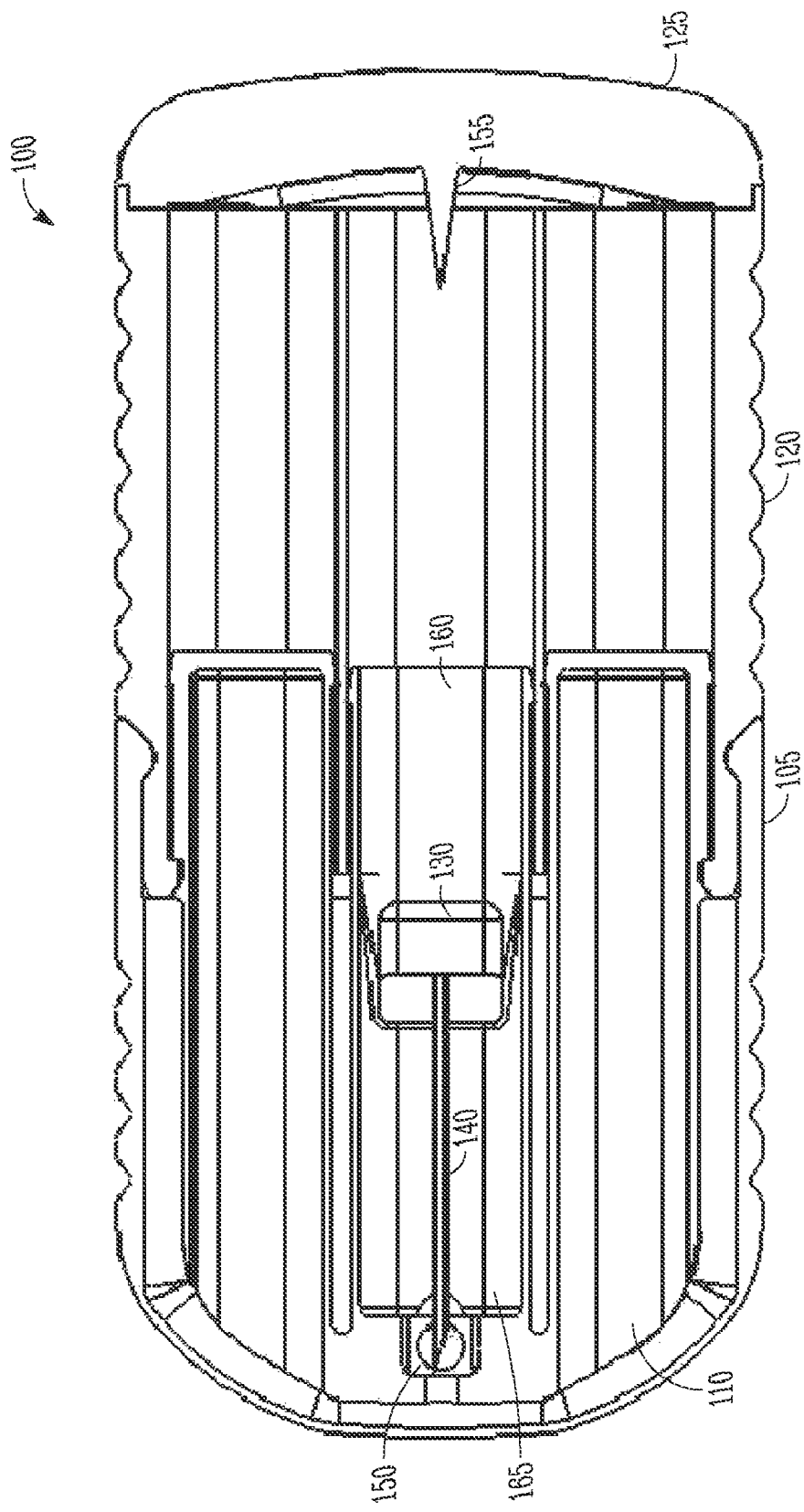

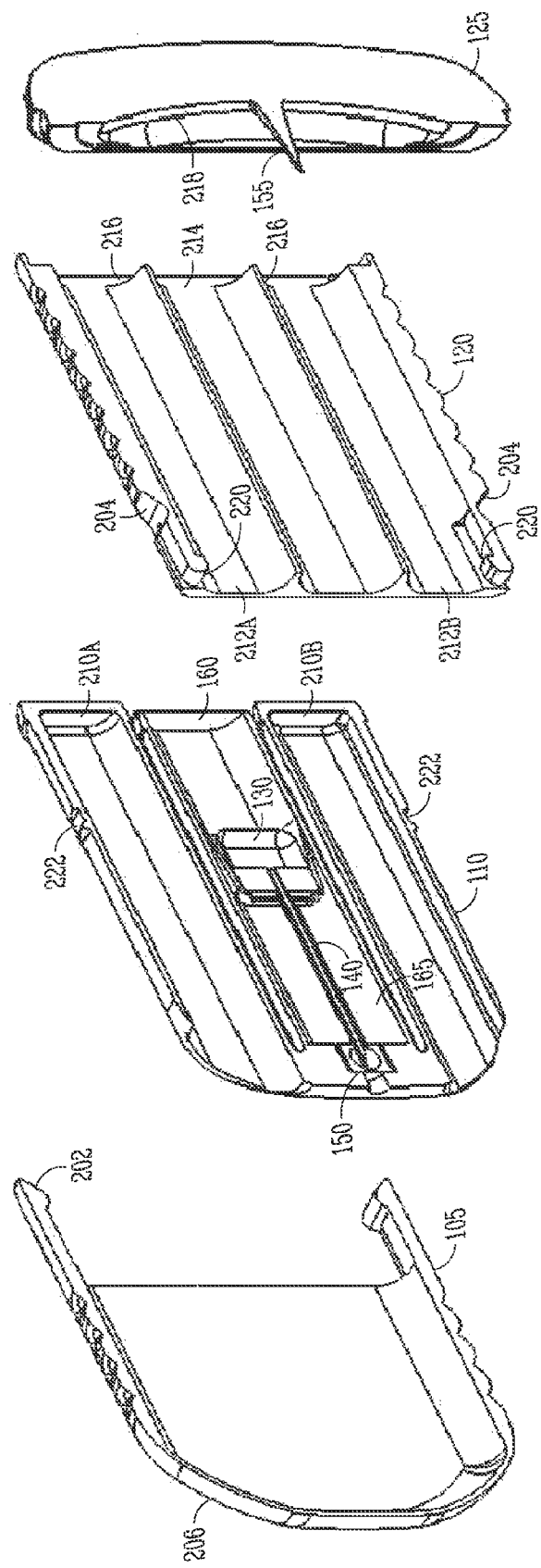

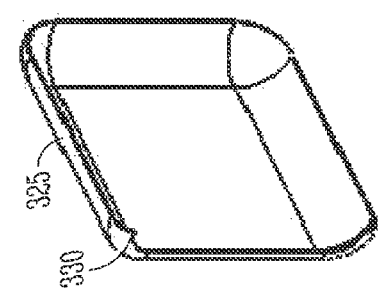
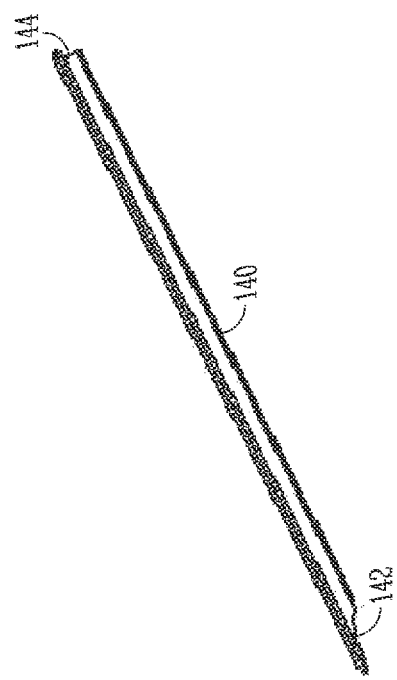
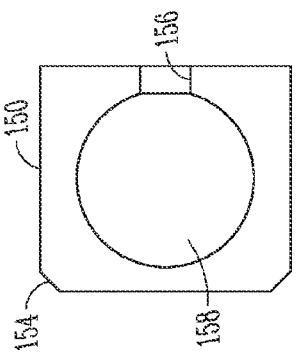
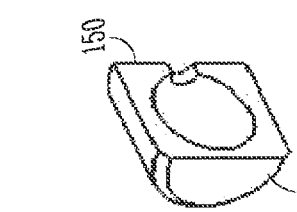

PNEUMATIC INJECTOR

CROSS-REFERENCE TO RELATED APPLICATIONS

The present application claims the benefit under 35 U.S.C. 119(e) of U.S. Provisional Application Ser. No. 61/043,268, filed Apr. 8, 2008, which is incorporated herein by reference in its entirety.

TECHNICAL FIELD

This document pertains generally to medical devices, and more particularly, but not by way of limitation, to a pneumatic injector.

BACKGROUND

Current rescue devices are inadequate. Such devices are generally too large to carry conveniently and the widely varying storage environments negatively affect potency longevity.

OVERVIEW

An example includes an auto-injector having a housing with a pneumatic cylinder. A piston located in the cylinder is coupled to a nose piece. A passage couples the cylinder and a conduit. A needle carrier is located within a member and the member is within the conduit. An hypodermic needle is affixed to the needle carrier. A diaphragm, also coupled to a portion of the nose piece, isolates the needle carrier from pressure within the conduit. An end cap affixed to a housing includes a spike. The spike is configured to pierce the diaphragm.

A guide affixed to a portion of the nose piece supports an end of the hypodermic needle. The needle carrier holds a fluid reservoir for storing a medicament.

In one example, the conduit is located between, and in parallel alignment with, two flanking cylinders and the nose piece carries two corresponding pistons.

After having removed the cover, a user can self-inject by swiftly thrusting the nose piece against the injection site. Movement of the piston relative to the housing causes air to be compressed in the cylinder, the passage, and in the conduit. At a predetermined relative position of the nose piece, the spike ruptures the diaphragm. Upon rupturing of the diaphragm, the pressure developed in the conduit is released to the member and a pressure is applied to the needle carrier. The pressure causes the needle carrier, and the needle, to travel in the member. The needle passes through the guide and into the injection site. The needle carrier travel is limited by the nose piece. Upon reaching the travel limit, the compressed air collapses the fluid reservoir, thus discharging the contents through the needle. After discharge, the needle can be safeguarded by replacement of the cover on the housing. In one example, the needle is retracted back within the nose piece before installing the cover.

This overview is intended to provide an overview of one example of the present subject matter. It is not intended to provide an exclusive or exhaustive explanation. The detailed description is included to provide further information.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 1 includes a perspective section view of a device.

FIG. 2A includes a perspective section view of a cover of a device.

FIG. 2B includes a perspective section view of a nose piece of a device.

FIG. 2C includes a perspective section view of a housing of a device.

FIG. 2D includes a perspective section view of an end cap of a device.

FIG. 4A includes a perspective section view of a shuttlecock of a device.

FIG. 4B-1 includes a perspective section view of a guide of a device.

FIG. 4B-2 includes a section view of a guide of a device.

FIG. 4C includes a perspective section view of a needle of a device.

FIG. 4D includes a perspective section view of a block of a device.

FIG. 4E includes a perspective section view of a reservoir of a device.

DETAILED DESCRIPTION

Figure 3A:
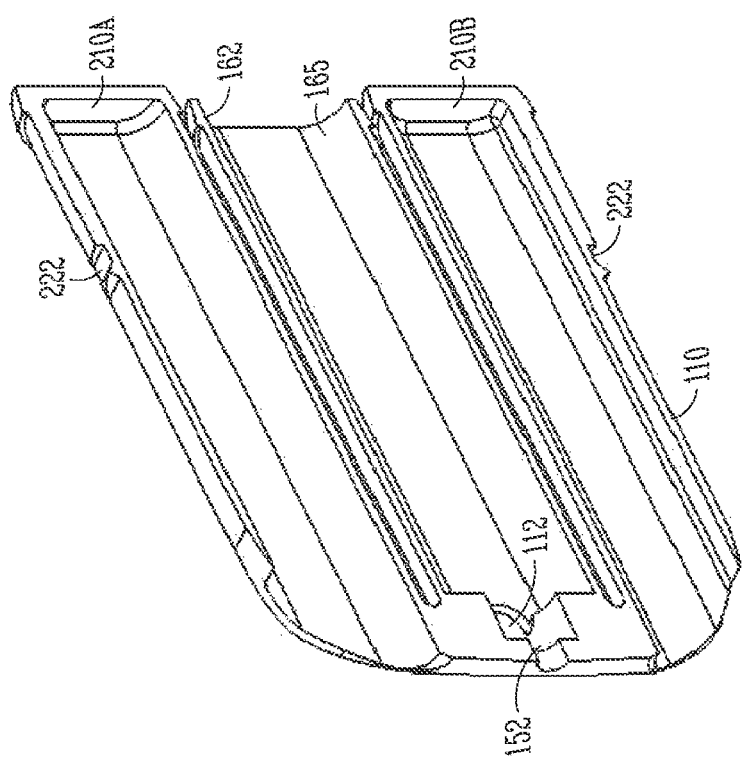
FIG. 3A includes a perspective section view of a nose piece of a device.

FIG. 1 includes a perspective section view of device 100. Device 100, in the example illustrated, includes (among other things) cover 105, nose piece 110, housing 120, and end cap 125.

In the example shown, the overall dimensions of the device, with cover 105 in position, is approximately 2.9 inches long by 1.375 inches wide and 0.25 inches high. For comparison, a typical credit card is about 3.375 inches by 2.125 inches by 0.030 inches and a typical cigarette lighter is approximately 0.5 inches thick. It is believed that the present subject matter can be readily carried in a pants pocket.

Cover 105 is configured to mate with a complementary feature of housing 120. Cover 105 is fabricated of molded plastic. Cover 105 is configured to enclose nose piece 110. An interlocking feature of cover 105 engages with a corresponding element of housing 120. With little force, a user can readily separate cover 105 from housing 120, thus exposing nose piece 110.

Nose piece 110, in the example illustrated, includes two pistons coupled by a rigid structure. The rigid structure also is coupled to member 165 in which needle carrier 130 travels. Needle carrier 130 carries needle 140. The rigid structure also includes a vent hole (not visible in this figure) and receiver for guide 150. Diaphragm 160 is disposed across an end of member 165. Nose piece 110 is fabricated of molded plastic.

Housing 120 includes two cylinders in which the pistons of nose piece 110 travel. The two cylinders flank a conduit for the member. The two cylinders and the conduit are in parallel alignment. The walls of the two cylinders are configured to form a passage in which compressed air in the cylinders is communicated to the member traveling in the conduit. Housing 120 is fabricated of molded plastic.

End cap 125 is configured to mate with housing 120. End cap 125 includes a void that serves as an internal passage for communicating compressed air. End cap 125 includes spike 155 configured to rupture diaphragm 160 at an end of the member. End cap 125 is fabricated of molded plastic.

FIG. 2A includes a perspective section view of cover 105 of device 100. As illustrated, cover 105 includes interlocking feature 202. An exterior surface of cover 105 includes detailing to enable a user to easily grip and remove cover 105 from engagement with housing 120.

In the normal service of device 100, needle 140 is substantially extended from nose piece 110. Following usage of device 100, cover 105 can be snapped into a position to enclose the end of housing 120. Following usage and installation of cover 105, needle 140 can remain in the extended position or needle 140 can be retracted. Needle 140 can be retracted by grasping along its length or by pushing at an end of the needle using, for example, region 206 of cover 105. Cover 105 is configured to substantially encase nose piece 110 when fitted to housing 120.

FIG. 2B includes a perspective section view of nose piece 110 of device 100. Nose piece 110 is configured to slidably engage with structure of housing 120.

In the example illustrated, nose piece 110 is held in an extended position by engagement of catch 220 (of housing 120) and stop 222 (of nose piece 110). The engagement of catch 220 and stop 222 can be readily overcome by a slight compressive force applied to nose piece 110. Having disengaged catch 220 and stop 222, nose piece 110 can be fully seated, limited by the wall structure of cylinder 212A and cylinder 212B and the depth of the slots separating piston 210A and piston 210B from member 165. As such, nose piece 110 can be viewed as having a variable location between first position (engagement of catch 220 and stop 222) and a second position (fully seated with housing 120).

Needle 140 is coupled to needle carrier 130. Needle carrier 130 lies within member 165. Needle carrier 130 can have a variable position within member 165 with a first position, as shown, wherein a tip of needle 140 lies within guide 150, and a second position wherein needle 140 is extended from nose piece 110 and needle carrier 130 has bottomed on internal structure of member 165 adjacent to guide 150 and a different portion of needle 140 lies within guide 150.

Diaphragm 160 is bonded to an end surface of member 165.

FIG. 2C includes a perspective section view of housing 120 of device 100. Housing 120 has an external surface with details to facilitate grasping by a user. Housing 120 also includes catch 220 that can be deflected to enable engagement of housing 120 with nose piece 110. In addition, housing 120 includes feature 204 configured to engage with retainer 202 of cover 105. In the figure, cylinder 212A and cylinder 212B and conduit 214 have a similar bore profile. Cylinder 212A, cylinder 212B, and conduit 214 are open ended and are configured to mate with piston 210A, piston 210B, and member 165, respectively. The walls of cylinder 212A, cylinder 212B, and conduit 214 have radiused corners to facilitate efficient sealing along the length of the walls.

While diaphragm 160 remains intact, member 165 operates like a piston operating in a cylinder. In this document, the cylinder is referred to as conduit 214. Relative movement of member 165 within conduit 214 can compress the air within conduit 214. Upon rupture of diaphragm 160 (by spike 155), member 165 no longer functions as a piston and the compressed air within conduit 214 is applied to the interior structure of member 165. The interior structure of member 165 includes needle carrier 130. While diaphragm 160 is breached, member 165 operates like a cylinder. While functioning as a cylinder, the compressed air within member 165 causes needle carrier 130 (along with needle 140) to travel to an extended position, thus ejecting the needle. Needle carrier 130 can be construed as a piston that carries needle 140. Member 165 can be referred to as a channel.

A portion of housing 120 is configured to mate with end cap 125.

FIG. 2D includes a perspective section view of end cap 125 of device 100. End cap 125 includes spike 155 and passage 218. Spike 155 has a sharp end configured to pierce diaphragm 160. Passage 218 provides an airway through which compressed air in cylinder 212A and in cylinder 212B is communicated to conduit 214, and thus to member 165. End cap 125 is fabricated of molded plastic and is fixedly mounted on an end of housing 120. In one example, end cap 125 is adhesively bonded to housing 120 at region 216.

FIG. 3A includes a perspective section view of nose piece 110 of device 100. In the figure, vent 112 is shown in a location near an end of member 165. Vent 112 equalizes the internal pressure on the needle-side of needle carrier 130 to atmospheric pressure. As needle carrier 130 travels to extend needle 140, the air within member 165 flows outward through vent 112.

Piston 210A and piston 210B are configured to form a seal with the interior surfaces of the walls of the respective cylinders. In addition, piston 210A and piston 210B are free to slide along the length of the respective cylinders.

An end of member 165 includes surface 162. In one example, diaphragm 160 is affixed to surface 162 with an adhesive bond. In one example, surface 162 is flat and lies in a plane oriented substantially perpendicular to the direction of travel of needle carrier 130.

Figure 3B:
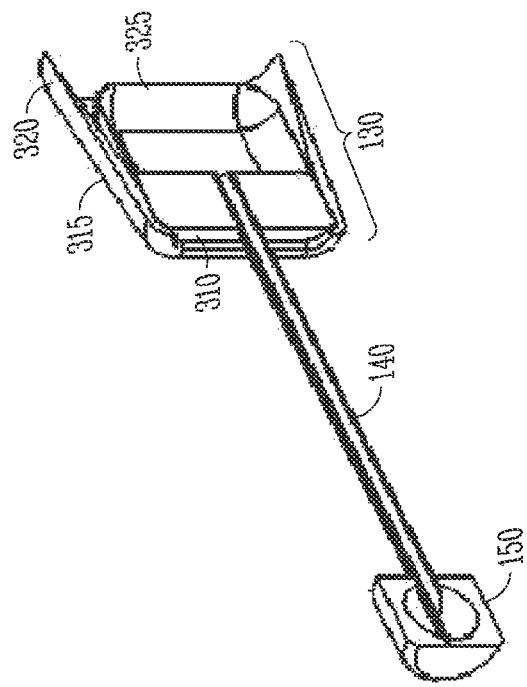
FIG. 3B includes a perspective section view of a needle of a device.

FIG. 3B includes a perspective section view of needle 140 of device 100. In the figure, a tip of needle 140 is coupled to guide 150 and an end of needle 140 is coupled to needle carrier 130. Needle carrier 130, shown with assembled components, includes block 310, shuttlecock 315, and reservoir 325. Shuttlecock 315 includes skirt 320 which is configured to slidably seal with the interior walls of member 165.

Figure 3C:
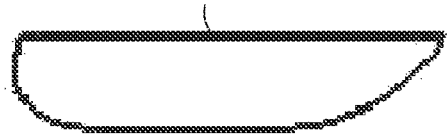
FIG. 3C includes a perspective section view of a diaphragm of a device.

FIG. 3C includes a perspective section view of diaphragm 160 of device 100. Diaphragm 160 is fabricated of a thin section of material that can sustain a differential air pressure and that readily fails when pierced. In one example, diaphragm 160 is fabricated of a membrane of cellophane or other plastic material.

FIG. 4A includes a perspective section view of shuttlecock 315 of device 100. Shuttlecock 315 is fabricated of a molded plastic. In one example, shuttlecock 315 is fabricated of a flexible material, such as nylon, and is crimped or wedge-locked in position over block 310 and reservoir 325.

Shuttlecock 315 includes lip 317 and skirt 320. Shuttlecock 315 is configured to slidably engage block 310 and retain reservoir 325 in a fixed position. A wall section of shuttlecock 315 includes an interference detail that allows shuttlecock 315 to snap into a fixed position over the underlying structure. Lip 317 captivates shuttlecock 315 on block 310. In one example, a wall thickness of skirt 320 is configured to expand and form an air seal against the interior walls of member 165 when a pressure is applied. As such, skirt 320 is sufficiently flexible to assure positive movement of the needle carrier when subjected to a differential pressure.

FIG. 4B-1 includes a perspective section view of guide 150 of device 100 and FIG. 4B-2 includes a section view of guide 150. Guide 150 is fabricated of an elastomeric material and, in the example illustrated, in the form of a cylinder having parallel bases. One base includes chamfer 154 and the other base includes aperture 156. Void 158 is spherical and substantially centered within the body dimensions of guide 150. The wall thickness at aperture 156 and the wall thickness at the chamfered base are configured to allow needle 140 to pass with low frictional resistance. Aperture 156 is configured to provide a fluid seal on the shaft of needle 140 and void 158 is configured to retain any fluid that may drip from the end of needle 140.

FIG. 4C includes a perspective section view of needle 140 of device 100. Needle 140 includes a sharp tip 142, end 144, and an internal bore or lumen. Tip 142 is configured to pierce the chamfered base of guide 150 as well as the tissue at the injection site. End 144 is configured normal to an axis of needle 140. In one example, needle 140 is fabricated of a surgically sterile metal such as stainless steel.

FIG. 4D includes a perspective section view of block 310 of device 100. Block 310 is fabricated of molded plastic and includes orifice 312. Orifice 312 is bonded to needle 140 at end 144. In the example illustrated, block 310 is configured as a rounded rectangular shaped solid. In one example, block 310 is insert-molded onto needle 140.

FIG. 4E includes a perspective section view of reservoir 325 of device 100. Reservoir 325 is fabricated of an elastomeric material, such as a sterile, epinephrine-compatible polymer balloon, and includes mouth 330. When assembled, mouth 330 is stretched over block 310 and shuttlecock 315 is snapped in position to retain reservoir 325 and resist separation. Reservoir 325 carries the fluid to be injected and is configured for a particular dosage. Reservoir 325 is sufficiently flexible that an air pressure will discharge the contents of reservoir 325 into the bore of needle 140. In one example, reservoir 325 is configured to hold a medicament and configured to collapse and discharge any contents under application of a compressive pressure. Reservoir 325 can be viewed as a collapsible chamber.

Figure 5:
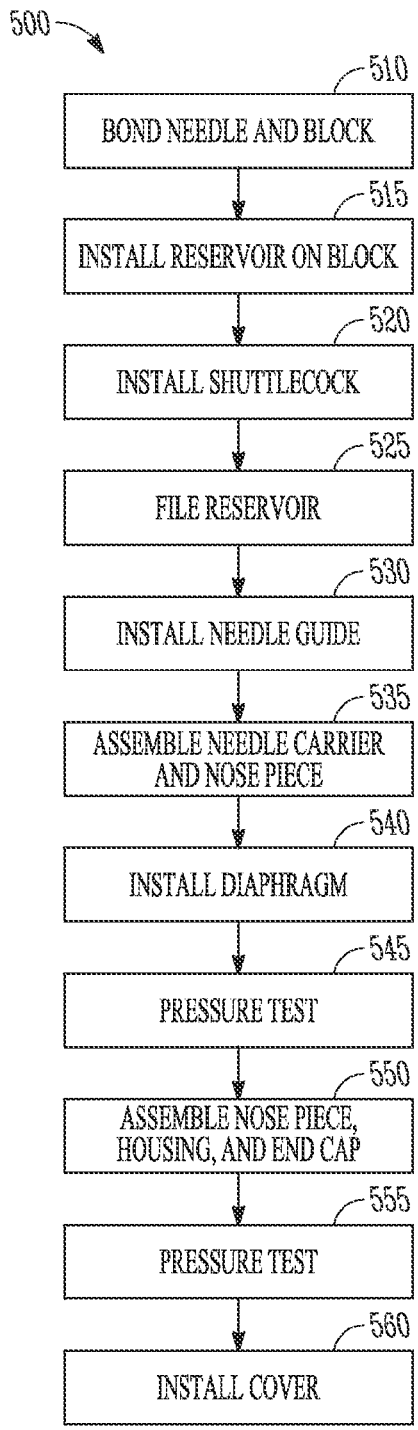
FIG. 5 includes a method of manufacturing a device.

FIG. 5 includes method 500 for manufacturing device 100. At 510, method 500 includes bonding needle 140 and block 310. In various examples, this includes forming an adhesive bond or molding block 310 directly on needle 140.

At 515, reservoir 325 is installed on block 310. This can include stretching reservoir 325 over block 310 in a manner similar to installing a balloon on a filling nozzle. The elasticity of the reservoir establishes a fluid tight seal on the external surfaces of block 310.

At 520, shuttlecock 315 is installed. Skirt 320 of shuttlecock 315 is passed over block 315 and snapped into position by a detail formed on an interior surface of shuttlecock 315. In one example, shuttlecock 315 is retained in position without need of an adhesive.

At 525, reservoir 325 is filled. Filling can include manual or automated manipulation of reservoir 325 at a time when tip 142 of needle 140 is immersed in fluid. For example, tip 142 can be injected in a septum of an inverted vial and by repeatedly squeezing reservoir 325 and releasing reservoir 325, air is exhausted and the contents of the vial are drawn into reservoir 325.

At 530, guide 150 is positioned on tip 142 of needle 140. This can include piercing a wall of guide 150 or insertion of tip 142 in a hole formed in a wall of guide 150.

At 535, needle carrier 130 and nose piece 110 are assembled. This can include placing guide 150 in guide receiver 152 formed in nose piece 110, as shown in the various figures. In addition, this can include positioning needle carrier 130 within member 165.

At 540, diaphragm 160 is bonded to surface 162 of nose piece 110. The adhesive used for bonding diaphragm 160 can include a cyanoacrylate adhesive or other type of adhesive.

At 545, a first pressure test is conducted to establish that diaphragm 160 is properly bonded to member 165. A pressure test can, for example, detect a leak in the joint between diaphragm 160 and member 165. Pressure testing can entail applying a predetermined air pressure and monitoring for evidence of leakage.

At 550, nose piece 110, housing 120, and end cap 125 are assembled. This can include engaging cylinder 212A with piston 210A, engaging cylinder 212B with piston 210B, and engaging member 165 with conduit 214 in the manner illustrated. In the example illustrated, nose piece 110 and housing 120 are assembled together without an adhesive. In the example illustrated, end cap 125 is assembled to housing 120 with an adhesive bond.

At 555, a second pressure test is conducted to establish that the assembled structure is properly configured. Pressure testing can entail applying a predetermined air pressure and checking for evidence of leakage as well as proper movement of the various components.

At 560, cover 105 is installed over nose piece 110 and onto housing 120. Cover 105 is assembled without adhesive and using a friction fit.

Figure 6:
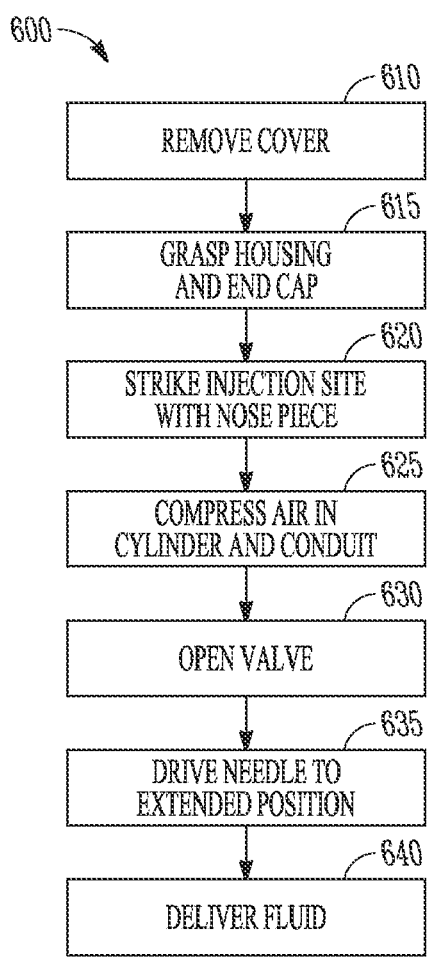
FIG. 6 includes a method of using a device.

FIG. 6 includes method 600 for using device 100. At 610, method 600 includes removing cover 105 from device 100. The user can remove this by overcoming the friction fit. A textured or detailed exterior surface of cover 105 and exterior surface of housing 120 facilitates the user's grip and, in one example, a color difference serves to readily identify the parting line for separating these components. Having removed cover 105 from an unused device, needle 140 will remain retracted within the structure of nose piece 110 and the tip will be positioned within guide 150.

At 615, the user grasps housing 120, along with end cap 125, and positions the device near the target injection site.

At 620, the user strikes the injection site with the exposed portion of nose piece 110 using a sharp blow. With such a force, nose piece 110 will break free of the position captivated by catch 220 and stop 222 and recede into the structure of housing 120.

At 625, the relative movement of the cylinder 212A with piston 210A, cylinder 212B with piston 210B, and member 165 with conduit 214, will cause compression of the air within cylinder 212A, cylinder 212B, and conduit 214.

At 630, continued travel of nose piece 110 relative to housing 120 will cause a valve to be opened. In the example illustrated, the valve is formed by diaphragm 160 and spike 155. Spike 155 will breach diaphragm 160 and allow the pressurized air in conduit 214 to flow into member 165.

At 635, needle 140 is driven to an extended position by the difference in air pressure present within member 165 and in the surrounding atmosphere. The surrounding atmosphere is present on the needle side of needle carrier 130 by virtue of vent 112. The differential air pressure is sufficient to drive needle 140 through guide 150 as well as into the tissue at the injection site.

At 640, the fluid in reservoir 325 is delivered through needle 140. The fluid in reservoir 325 is expelled by the compressed air remaining in member 165 after needle carrier 130 has moved to the extended position.

Figure 7:
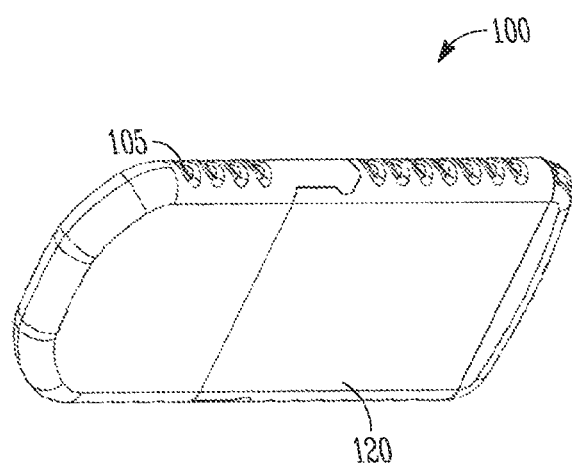
FIG. 7 includes a perspective view of a surface of a device.

FIG. 7 includes a perspective section view of a surface of device 100. In contrast to FIG. 1, FIG. 2, FIG. 3, and FIG. 4 (each of which illustrate selected internal elements in a section view), FIG. 7 illustrates an external view including cover 105 and housing 120. The section views of this document depict the various components with a cutting plane that corresponds to approximately a mid-line. FIG. 7 illustrates the molded details appearing on an outer edge. The molded details are configured to facilitate grasping of device 100.

FIG. 8 includes a sequence of images corresponding to a method of using device 100. The various figures identify selected elements including cover 105, nose piece 110, housing 120, needle 140, and diaphragm 160. In FIG. 8A, cover 105 has been removed in preparation for injecting a drug using device 100. Nose piece 110 remains in an extended position, needle 140 remains in a retracted position, and diaphragm 160 is intact.

Figure 8A:
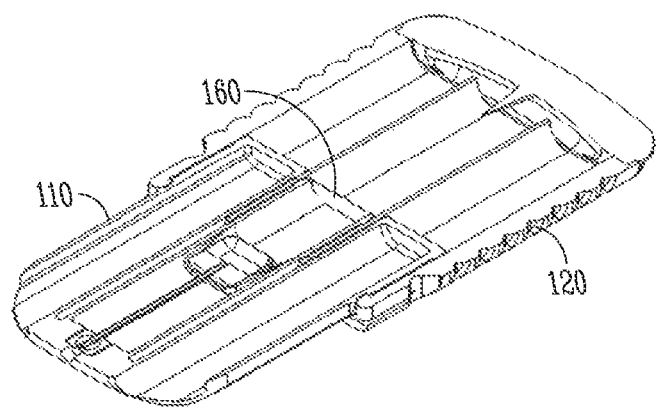
FIGS. 8A-8G include a sequence of device images.
Figure 8B:
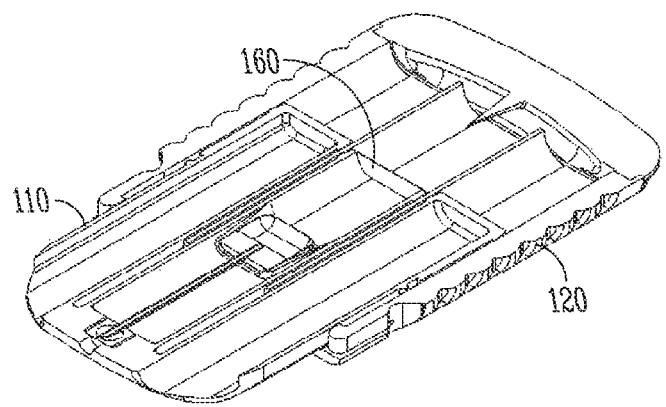

In FIG. 8B, nose piece 110 is shown partially retracted into housing 120. Air pressure inside the chambers of housing 120 is elevated above ambient pressure.

Figure 8C:
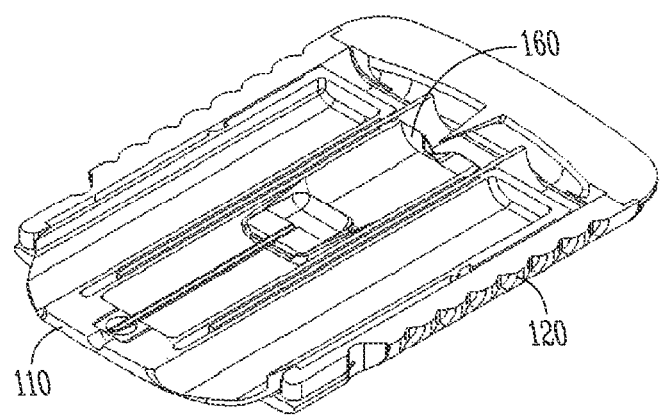

In FIG. 8C, nose piece 110 is shown nearly fully retracted and diaphragm 160 is beginning to rupture. At this point, air pressure within device 100 is at a maximum value.

Figure 8D:
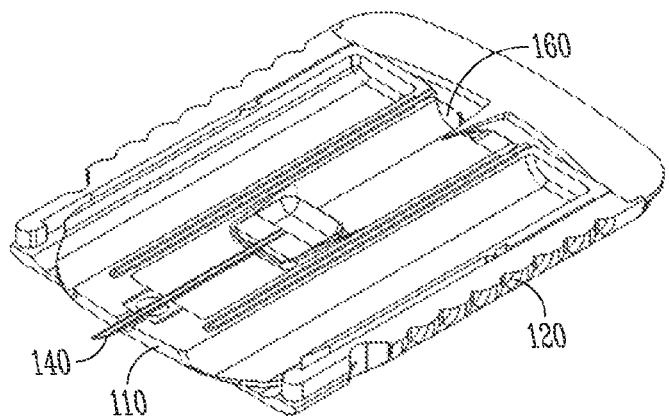

In FIG. 8D, nose piece 110 is shown fully retracted and diaphragm 160 has ruptured. Air pressure within device 100 is beginning to drop since needle 140 has started to move to an extended position. In the configuration shown, nose piece 110 would typically be in contact with an injection site and needle 140 would be partially inserted.

Figure 8E:
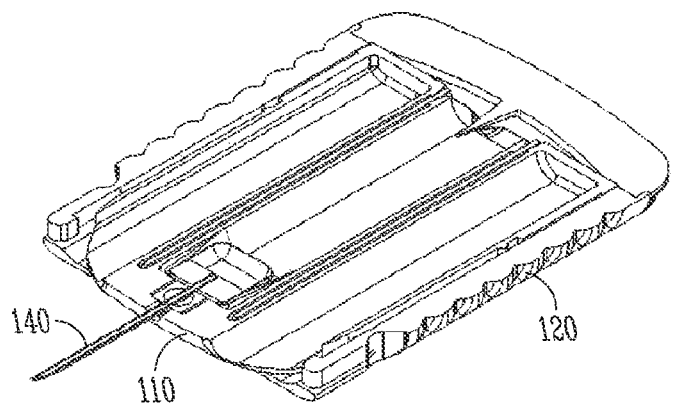

In FIG. 8E, nose piece 110 remains fully retracted and needle 140 is fully extended, having reached the end of its travel. Air pressure within device 100 remains elevated relative to ambient pressure.

Figure 8F:
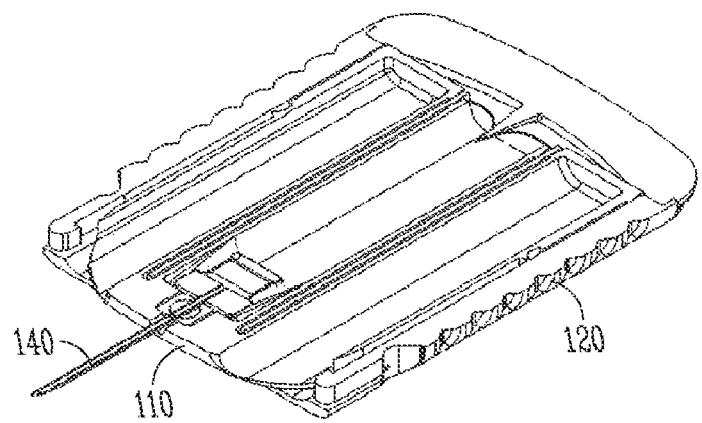

In FIG. 8F, the remaining air pressure within device 100 operates to collapse the reservoir and eject the contents via needle 140, thus injecting the site with the fluid.

Figure 8G:
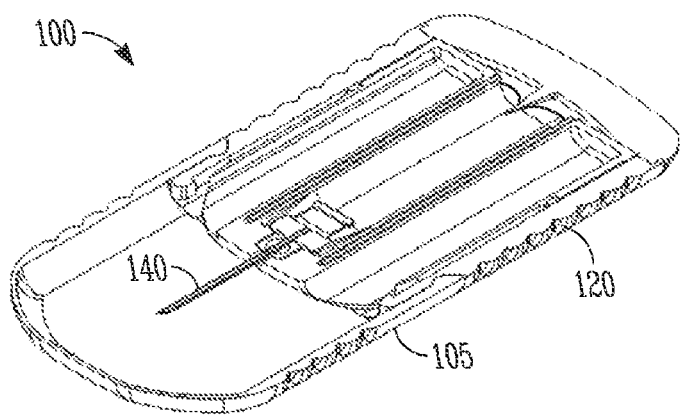

In FIG. 8G, the needle is manually withdrawn from the injection site and cover 105 is installed on housing 120. In this example, needle 140 remains in an extended position within the confines of cover 105. Nose piece 105 remains in the fully retracted position.

Additional Notes

In one example, after having filled reservoir 325 with the fluid, guide 150 is placed over tip 142. Guide 150 prevents contamination of tip 142, precludes evaporation, and retains fluid leakage from needle 140. When needle 140 is passing through guide 150, the walls of guide 150 collapse in a direction away from the needle. This reduces the drag force acting on the needle while the needle is advancing. Low drag force reduces the burden of injecting the needle.

In one example, skirt 320 of shuttlecock 315 is the only portion of needle carrier 130 in physical contact with member 165. This reduces the frictional drag of the needle travel and also enables a user to readily retract needle 140 after usage. The user can exert a force using cover 105 to drive needle 140 back into nose piece 110.

Cover 105 is configured to prevent accidental discharge. Cover 105 precludes relative movement of nose piece 110 and housing 120 and, in the absence of relative movement, a differential air pressure cannot be developed. In the absence of a differential air pressure, needle 140 will remain stationary.

The length of spike 155 and position of diaphragm 160 determine the point in the movement of nose piece 110 at which needle 140 travel commences. The needle delivery force increases linearly until diaphragm 160 is burst. When diaphragm 160 bursts, the internal pressure is applied to needle carrier 130 which drives needle 140 into, for example, the patient's leg, while the user completes the operating stroke. By bursting diaphragm 160 before the end of the stroke, the peak force required of the user is reduced. This also reduces the force that the user feels against their leg from the device. After nose piece 110 has reached the end of travel, the epinephrine is injected. The user then withdraws the device and installs cover 105 so that it can be safely discarded and avoid needle sticks. Thus, the length of spike 155 also affects the peak forces developed within the device.

In one example, needle carrier 130 is retained in a fixed position relative to member 165. For example, corresponding features of carrier 130 and member 165 can retain relative position until the motive pressure exceeds a predetermined value and carrier 130 commences travel down the length of member 165. A complementary feature can include a friction fit or a catch and stop assembly configured to stabilize carrier 130 and reduce movement until deliberately called for by action of a user.

In one example, spike 155 is configured to dislodge needle carrier 130 from a fixed position within member 165. For example, an extended portion of spike 155 can be configured to contact carrier 130 and overcome a retention feature or mechanism, thereby enabling carrier 130 to travel within the length of member 165.

In one example, different dosages are provided. The dosages can be determined, for example, by selecting a suitable size reservoir. In one example, the dosages are 0.1 ml, 0.2 ml, and 0.3 ml. In one example, different fill levels are used with a particular reservoir. The needle and needle carrier can include a color code or label to denote contents and dosages.

Additional methods can include testing for seal integrity. For example, the various sealed assemblies can be tested at different stages of fabrication.

The present subject matter can be configured for carrying in a pocket or in a convenient manner that may provide a more stable storage environment. For example, some drugs deteriorate rapidly with exposure to temperature extremes. By configuring the present subject matter for carrying in a pocket, the useful life of the product can be improved.

In one example, end cap 125 and housing 120 are formed as a single component and include through holes to communicate compressed air from cylinders to the conduit.

In one example, a feature within member 165 limits the travel of needle carrier 130. The feature, such as a stop, can limit forward or rearward travel of needle carrier 130.

In one example, guide 150 provides a fluid-tight seal closing on needle 140. The seal can include a self-sealing septum, and fabricated of various materials including polytetrafluoroethylene (PTFE), rubber or silicone.

Various elements shown in the figures and described herein can have different shapes and arrangements. For example, needle carrier 130 can have a circular, oval, or rounded rectangular cross section. In particular, needle carrier 130 and the interior bore of member 165 can be circular. In a similar manner, the exterior profile of member 165 as well as the interior bore of conduit 214 can be circular. Furthermore, piston 210A, piston 210B, cylinder 212A, and cylinder 212B can have a circular cross-section.

Figure 9:
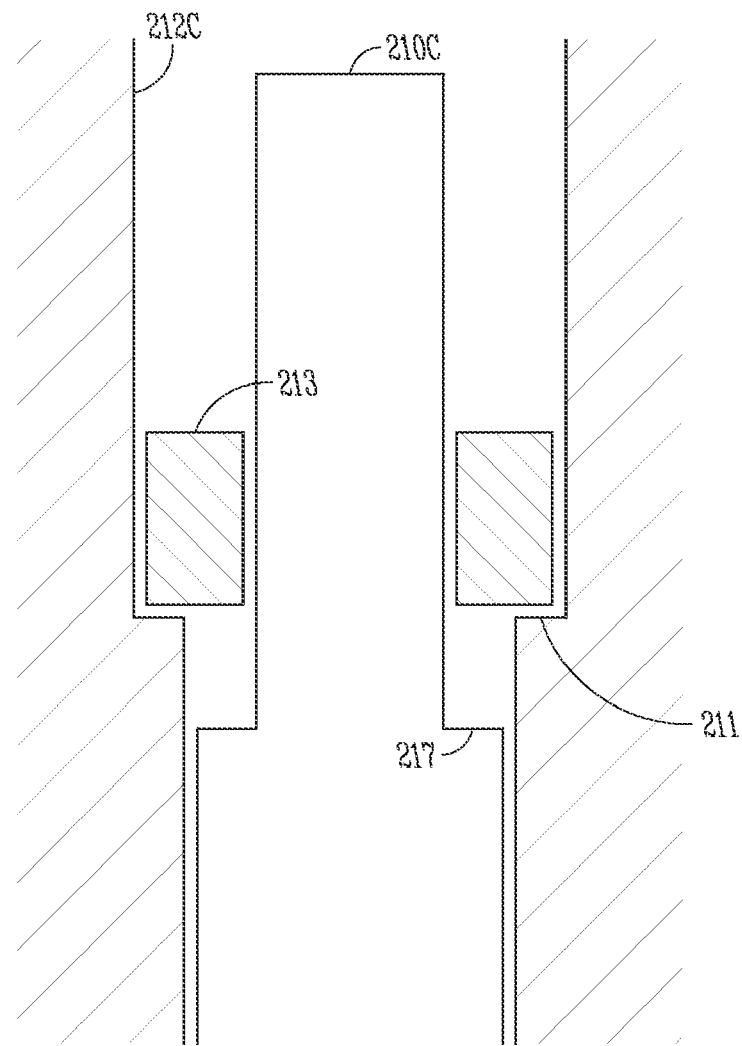
FIG. 9 includes a view of a piston and cylinder according to one example.

FIG. 9 illustrates a partial sectional view of an example of a complex piston arrangement. In the figure, cylinder 213C and piston 210C compares with cylinders 213A and 213B and pistons 210A and 210B of earlier figures, such as shown in FIGS. 2B and 2C. Cylinder 212C includes shoulder 211 and piston 210C includes shoulder 217. An aperture of sleeve 213 is fitted to a small diameter portion of piston 210C and the outer diameter of sleeve 213 is fitted within the large diameter of cylinder 212C. Shoulder 211 and shoulder 217 limit the travel of sleeve 213 relative to the cylinder 212C and piston 210C, respectively.

In one example, the upper portion of the figure corresponds to housing 120 and the lower portion of the figure corresponds to cover 105. In operation, user-action drives piston 210C in a direction toward the upper portion of the figure. The internal pressure increases linearly with the movement of piston 210C and is proportional to the area at the end of the piston. When shoulder 217 engages the lower surface of sleeve 213, the effective piston area is increased and internal pressure rises more rapidly. This arrangement of shoulders and the sleeve allows for increasing the internal pressure during selected portions of the device operation that may be more suitable for some applications.

The cylinders of the present subject matter can be air-filled (in which case, the device operates using pneumatic pressure), or fluid-filled (in which case, the device operates using a fluid pressure). The fluid can be a liquid such as water or other such fluid.

Additional Notes

The above detailed description includes references to the accompanying drawings, which form a part of the detailed description. The drawings show, by way of illustration, specific embodiments in which the present subject matter can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
a housing having a first cylinder, a second cylinder, and a third cylinder in fluid communication;
a nose piece having a first piston, a second piston, and a third piston corresponding to the first cylinder, the second cylinder, and the third cylinder, respectively, the second piston having an interior chamber and having a membrane configured to control fluid communication between the housing and the interior chamber; and
a needle assembly having a piston and a needle and having a position within the interior chamber determined by a pressure applied to the interior chamber.

2. The system of claim 1 wherein the needle assembly includes a medicament reservoir.

3. The system of claim 2 wherein the medicament reservoir includes a collapsible chamber.

4. The system of claim 1 wherein the needle assembly includes a skirt configured to slidably seal with a surface of the interior chamber.

5. The system of claim 1 wherein the needle assembly includes a guide member coupled to the nose piece.

6. The system of claim 1 wherein the housing includes a spike configured to rupture the membrane at a particular relative alignment of the housing and the nose piece.

7. The system of claim 1 further including a cover configured to engage a portion of the housing and enclose the nose piece.

8. The system of claim 1 wherein at least one of the first piston and the third piston includes a sleeve.

* * * * *